United States Patent
Plismy Juquel

(10) Patent No.: US 10,064,791 B2
(45) Date of Patent: Sep. 4, 2018

(54) COSMETIC COMPOSITION IN THE FORM OF AN OIL-IN-WATER EMULSION

(71) Applicant: L'OREAL, Paris (FR)

(72) Inventor: Fanny Plismy Juquel, Antony (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/648,773

(22) PCT Filed: Nov. 29, 2013

(86) PCT No.: PCT/IB2013/060506
§ 371 (c)(1),
(2) Date: Jun. 1, 2015

(87) PCT Pub. No.: WO2014/083541
PCT Pub. Date: Jun. 5, 2014

(65) Prior Publication Data
US 2015/0313810 A1    Nov. 5, 2015

Related U.S. Application Data

(60) Provisional application No. 61/735,280, filed on Dec. 10, 2012.

(30) Foreign Application Priority Data

Nov. 30, 2012   (FR) .................................... 12 61475

(51) Int. Cl.
*A61K 8/06* (2006.01)
*A61K 8/81* (2006.01)
*A61K 8/73* (2006.01)
*A61Q 19/00* (2006.01)

(52) U.S. Cl.
CPC ............... *A61K 8/062* (2013.01); *A61K 8/73* (2013.01); *A61K 8/8158* (2013.01); *A61Q 19/00* (2013.01); *A61K 2800/10* (2013.01); *A61K 2800/33* (2013.01); *A61K 2800/594* (2013.01); *A61K 2800/805* (2013.01)

(58) Field of Classification Search
CPC ........ A61K 8/062; A61K 8/73; A61K 8/8158; A61K 2800/10; A61K 2800/805; A61K 2800/33; A61K 2800/594; A61Q 19/00
See application file for complete search history.

(56) References Cited

U.S. PATENT DOCUMENTS

| | | | |
|---|---|---|---|
| 5,877,144 A | 3/1999 | Ehrhardt et al. | |
| 2002/0018758 A1 | 2/2002 | Hansenne et al. | |
| 2011/0034408 A1* | 2/2011 | Lorant ................. | A61K 8/8158 514/54 |
| 2011/0088711 A1* | 4/2011 | Bonafos ............... | A61K 8/0208 132/200 |

FOREIGN PATENT DOCUMENTS

| | | |
|---|---|---|
| EP | 2184048 A1 | 5/2010 |
| FR | 2843695 A1 | 2/2004 |
| FR | 2925361 A1 | 6/2009 |
| FR | 2927252 A1 | 8/2009 |
| RU | 2 180 212 C2 | 3/2002 |
| WO | 99/64549 A1 | 12/1999 |
| WO | 2009/080661 A2 | 7/2009 |

OTHER PUBLICATIONS

Rajinder Pal: Effect of Droplet Size on the Rheology of Emulsions, AIChE Journal, vol. 42, No. 11, Nov. 1996, pp. 3181-3190.*
Emulsion Viscosity and the Effect of Droplet Concentration: retrieved from internet: http://www.azom.com/article.aspx?ArticleID=12057. Retrieved on Apr. 18, 2017.*
Terminology of polymers and polymerization processes in dispersed systems (IUPAC Recommendations 2011): retrieved from internet: https://www.iupac.org/publications/pac/pdf/2011/pdf/8312x2229.pdf. Retrieved on Apr. 18, 2017.*
Booten, K. et al., "Polymeric, Carbohydrate-based Surfactants and their Use in Personal Care Applications," SOFW-Journal, vol. 130, No. 8, (2004), pp. 10 and 14-16.
Aug. 5, 2014 Search Report issued in International Patent Application No. PCT/IB2013/060506.
Aug. 5, 2014 Written Opinion issued in International Patent Application No. PCT/IB2013/060506.
Sep. 13, 2017 Office Action issued in Russian Application No. 2015124498/15(038304).

* cited by examiner

*Primary Examiner* — Hong Yu
(74) *Attorney, Agent, or Firm* — Oliff PLC

(57) ABSTRACT

The present invention relates to a cosmetic composition, in the form of an oil-in-water emulsion, characterized in that it comprises a 2-acrylamido-2-methylpropanesulfonic acid polymer, a copolymer of 2-acrylamido-2-methylpropanesulfonic acid and of an alcohol(meth)acrylate, and a hydrophobic-modified inulin-based amphiphilic polymer, the globules of the said emulsion having a mean size ranging from 15 to 500 microns and the oily phase being present in an amount of less than 35% by weight relative to the total weight of the composition. The invention also relates to a cosmetic process for treating keratin materials.

12 Claims, No Drawings

COSMETIC COMPOSITION IN THE FORM OF AN OIL-IN-WATER EMULSION

The present invention is directed towards proposing cosmetic compositions in the form of an oil-in-water emulsion, containing at least a 2-acrylamido-2-methylpropanesulfonic acid polymer, a copolymer of 2-acrylamido-2-methylpropanesulfonic acid and of an alcohol (meth)acrylate, and a hydrophobic-modified inulin-based amphiphilic polymer.

For various reasons associated in particular with greater comfort of use (softness, emollience and the like), current cosmetic compositions are usually in the form of an emulsion of the oil-in-water (O/W) type consisting of an aqueous dispersing continuous phase and an oily dispersed discontinuous phase, or of an emulsion of the water-in-oil (W/O) type consisting of an oily dispersing continuous phase and an aqueous dispersed discontinuous phase.

O/W emulsions are the ones most sought in the cosmetics field, since they comprise an aqueous phase as the external phase, which gives them, when applied to the skin, a fresher, less greasy and lighter feel than W/O emulsions.

Standard O/W emulsions are generally stabilized with amphiphilic molecules of low molar mass (<5000 g/mol), such as emulsifying surfactants of the alkylglycerol or alkylpolyoxyethylene type. These emulsions generally have an oil drop or oil globule size of the order of a micron.

Moreover, polymer-based emulsions comprising a hydrophilic part and a hydrophobic part consisting of a fatty chain, such as copolymers of $C_{10}$-$C_{30}$ alkyl acrylate and of acrylic or methacrylic acid, for instance the products sold under the name Pemulen TR1® and TR2® by the company Noveon, are known. These crosslinked polymers lead to emulsions comprising larger-sized drops (of about 10-15 μm).

However, these emulsions are difficult to stabilize in the case where it is desired to obtain fluid textures, since creaming of the emulsion takes place.

Formulations of this type are conventionally known as giant-drop emulsions.

Document FR-2 843 695 describes O/W emulsions containing an amphiphilic polymer of non-crosslinked 2-acrylamido-2-methylpropanesulfonic acid and an oil content of greater than 40% by weight. However such an amount of oily phase leads to a greasy and shiny effect during application to the skin, which the user may find unacceptable.

Moreover, O/W emulsions comprising an amphiphilic polymer, such as a 2-acrylamido-2-methylpropanesulfonic acid derivative, and an oil content of less than 30%, are known from FR 2 927 252. These compositions afford a non-greasy effect on the skin and are stable irrespective of their viscosity. However, for certain applications, the sensory aspect of these formulations is not entirely satisfactory. In particular, in terms of texture, although this giant-drop technique is advantageous as regards the soft, silky finish it affords, the drops have a texture that may be judged too thick and excessively slow penetration into the skin. In addition, they do not afford any freshness effect, which is a highly sought effect, obtained, for example, by means of formulations of serum type. The document EP 2 184 048 also describes O/W emulsions comprising an amphiphilic polymer, such as a 2-acrylamido-2-methylpropanesulfonic acid derivative. However, these compositions are not capable of affording a freshness effect when applying to the skin.

There is thus a need for oil-in-water emulsions, in particular containing "giant" drops, which have a light, fluid texture, which prove to be very easy to apply and which are also capable of affording a freshness effect, while at the same time conserving a non-greasy effect on the skin and a soft, silky finish.

In other words, there is a need to combine the advantages of the giant-drop technique with those of sera in sensory terms.

Unexpectedly, the inventors have found that such an objective may be achieved provided that specific compounds are combined in an oil-in-water emulsion containing giant drops. The texture was thus able to be improved.

The inventors have in point of fact found, surprisingly, that the combination in an oil-in-water emulsion of at least one 2-acrylamido-2-methylpropanesulfonic acid polymer, of a copolymer of 2-acrylamido-2-methylpropanesulfonic acid and of an alcohol (meth)acrylate, and of a hydrophobic-modified inulin-based amphiphilic polymer, and of which the mean drop size is between 15 and 500 μm, satisfies these needs.

Thus, the present invention relates to a cosmetic composition, in the form of an oil-in-water emulsion, characterized in that it comprises at least a 2-acrylamido-2-methylpropanesulfonic acid polymer, a copolymer of 2-acrylamido-2-methylpropanesulfonic acid and of an alcohol acrylate or an alcohol methacrylate, and a hydrophobic-modified inulin-based amphiphilic polymer, the globules of the said emulsion having a mean size ranging from 15 to 500 microns and the oily phase being present in an amount of less than 35% by weight relative to the total weight of the composition.

A composition according to the invention is advantageous in several respects.

Firstly, the composition according to the invention has the advantage of having good harmlessness and good cosmetic properties, i.e. a uniform and pleasant texture on application. In addition, it is stable over time.

An emulsion is stable if no change in its macroscopic or microscopic appearance and in its physicochemical characteristics (drop size, pH, viscosity) is observed after storage at various temperatures (T=4° C., $T_{room}$, 40° C. and 45° C.) for a duration of 2 months.

In addition, this combination gives access to a combination that may be likened to a texture said to have a "quick-break" effect.

Thus, when the composition as defined above is applied to keratin materials, its structure breaks, giving a pleasant freshness effect known as the "quick break".

Such a product satisfies the expectations of potential users who are not satisfied at the present time with the sensory performance qualities manifested by the current products.

Thus, as emerges from the text hereinbelow, and more particularly from the examples, the compositions according to the invention prove to be particularly advantageous with regard to the sensory feeling that they give the user at the time of application.

During the application to the surface of the keratin material, the texture of the composition breaks under the effect of the shear generated during its spreading by the user onto the surface of the keratin materials, then affording an immediate fresh effect.

As regards the sensory feeling, the compositions according to the invention prove to be soft and light to the touch and have a glidant nature which makes them easy to apply.

The composition according to the invention is intended for topical application: it contains a physiologically acceptable medium, i.e. a medium that is compatible with keratin materials.

The term "topical application" means herein an external application to keratin materials, which are especially the skin, the scalp, the eyelashes, the eyebrows, the nails, mucous membranes and the hair.

The term "physiologically acceptable medium" is intended to denote a medium which is particularly suitable for the application of a composition of the invention to the skin and/or the lips.

The physiologically acceptable medium is generally adapted to the nature of the support onto which the composition has to be applied, and also to the appearance under which the composition has to be packaged.

According to another of its aspects, a subject of the invention is also a process for making up and/or caring for a keratin material, in particular the skin, comprising at least a step that consists in applying to the said keratin materials a composition in accordance with the invention.

Globules

In the present invention, the term "mean size of the oil globules" means the effective volume-mean diameter D[4.3] of the said globules, as measured by static light scattering using a commercial particle size analyser such as the MasterSizer 2000 from Malvern. The data are processed on the basis of the Mie scattering theory. This theory, which is exact for isotropic particles, makes it possible to determine, in the case of non-spherical particles, an effective particle diameter. This theory is especially described in the publication by Van de Hulst, H. C., "*Light Scattering by Small Particles*", Chapters 9 and 10, Wiley, New York, 1957.

The "effective" volume-mean diameter D[4.3] is defined in the following manner:

$$D[4.3] = \frac{\Sigma_i V_i \cdot d_i}{\Sigma_i V_i}$$

where $V_i$ represents the volume of the particles of effective diameter $d_i$. This parameter is in particular described in the technical documentation of the particle size analyser.

The measurements are performed at 25° C. after diluting the composition by a factor of greater than 100 with osmosed water.

The "effective" diameter is obtained by specifying the refractive indices of water and of the fatty phase as a function of its nature.

The mean size of the oil globules may range from 15 to 500 µm, preferentially from 15 to 300 µm and better still from 15 to 150 µm.

The emulsions according to the invention are translucent: in particular, they have a light transmittance at a wavelength equal to 500 nm, through a sample 50 µm thick, at least 1.5 times higher than that of an emulsion of the same composition in which the drop diameter is less than 15 µm.

The transmittance is measured using a Carry 600 UV-visible spectrophotometer at a wavelength equal to 500 nm. The emulsion is placed between two quartz slides, one of which comprises a notch 50 microns deep.

The viscosity of the dispersions obtained may range from very fluid (spray) to very viscous (cream) and it is adjusted especially as a function of the content of introduced polymers and of the content of emulsified oily phase.

The composition of the invention has a viscosity that may range, for example, from 0.01 Pa·s to 100 Pa·s at a temperature of 25° C., the viscosity being measured using a Rheomat 180 machine (from the company Lamy), equipped with an MS-R1, MS-R2, MS-R3, MS-R4 or MS-R5 spindle chosen as a function of the consistency of the composition, rotating at a spin speed of 200 rpm.

Amphiphilic Polymers

The term "amphiphilic polymer" means a polymer which comprises at least one hydrophilic part (or block) and at least one hydrophobic part (or block). This polymer is water-soluble or water-dispersible.

The term "water-soluble or water-dispersible" polymer refers to a polymer which, when introduced into water at a concentration equal to 1%, gives a macroscopically homogeneous solution whose light transmittance, at a wavelength equal to 500 nm, through a sample 1 cm thick, is at least 10%, which corresponds to an absorbance [abs=−log(transmittance)] of less than 1.5.

The term "amphiphilic polymer" also means a polymer which, when introduced into an aqueous solution at 0.05% (by weight), makes it possible to reduce the surface tension of water at 25° C. to a value of less than 50 mN/m and preferably less than 40 mN/m.

The amphiphilic polymers under consideration in the composition according to the invention are the 2-acrylamido-2-methylpropanesulfonic acid polymer, the copolymer of 2-acrylamido-2-methylpropanesulfonic acid and of an alcohol (meth)acrylate and the hydrophobic-modified inulin-based amphiphilic polymer, described below.

They have the advantage of allowing the dispersion of oils of any nature, which may equally be oils constituted by triglycerides or alkanes, esters, silicones, sunscreens or perfluoro oils, either alone or as mixtures.

2-Acrylamido-2-methylpropanesulfonic acid polymer

As stated above, the composition according to the invention comprises at least one 2-acrylamido-2-methylpropanesulfonic acid polymer.

The 2-acrylamido-2-methylpropanesulfonic acid polymer that may be used in the composition according to the invention comprises 2-acrylamido-2-methylpropanesulfonic acid units of formula (I) below:

$$\text{(I)}$$

in which X+ is a proton, an alkali metal cation, an alkaline-earth metal cation or an ammonium ion.

As 2-acrylamido-2-methylpropanesulfonic acid polymer that may be used in the composition according to the invention, mention may be made in particular of the product sold by the company Clariant under the name Hostacerin® (INCI name: ammonium polyacryldimethyltauramide).

Preferably, the amount of 2-acrylamido-2-methylpropanesulfonic acid polymer as active material in the composition of the invention may range from 0.01% to 5% by weight, preferably from 0.05% to 3% by weight and better still from 0.1% to 1% by weight relative to the total weight of the composition.

Preferably, the ratio of the amount of oily phase to the amount of 2-acrylamido-2-methylpropanesulfonic acid polymer as active material may range from 40 to 200 and preferably from 50 to 120.

Copolymer of 2-acrylamido-2-methylpropanesulfonic acid and of an alcohol methacrylate or acrylate The composition according to the invention comprises, besides the 2-acrylamido-2-methylpropanesulfonic acid polymer described above, at least one copolymer of 2-acrylamido-2-methylpropanesulfonic acid and of an alcohol methacrylate or acrylate.

The copolymers of 2-acrylamido-2-methylpropanesulfonic acid and of an alcohol (meth)acrylate according to the invention give stable emulsions and are in very varied textures, ranging from a sprayable fluid to a cream with very good cosmetic qualities. These copolymers also have the advantage of being sparingly sensitive to pH variations for values of between 4 and 8, which are the usual values for cosmetic compositions.

As copolymers of 2-acrylamido-2-methylpropanesulfonic acid and of an alcohol (meth)acrylate that may be used in the composition according to the invention, examples that may be mentioned include polymers comprising:
(a) from 80 mol % to 99 mol % of 2-acrylamido-2-methylpropanesulfonic acid units of formula (I) below:

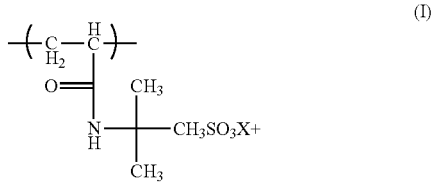

in which $X^+$ is a proton, an alkali metal cation, an alkaline-earth metal cation or an ammonium ion; and
(b) from 1 mol % to 20 mol % and preferably from 1 mol % to 15 mol % of units of formula (II) below:

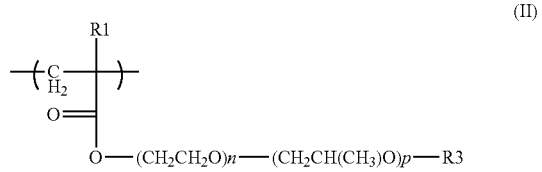

in which n and p, independently of each other, denote an integer ranging from 0 to 30 and preferably from 1 to 20, with the proviso that n+p ranges from 1 to 30, better still from 6 to 25, and preferably p is equal to 0; $R_1$ denotes a hydrogen atom or a linear or branched $C_1$-$C_6$ alkyl radical (preferably methyl) and $R_3$ denotes a linear or branched alkyl group comprising m carbon atoms, with m ranging from 6 to 30 and preferably from 10 to 25 carbon atoms.

Preferably, the copolymer of 2-acrylamido-2-methylpropanesulfonic acid and of an alcohol (meth)acrylate is a copolymer of 2-acrylamido-2-methylpropanesulfonic acid and of a $C_{10}$-$C_{22}$ alcohol (meth)acrylate comprising from 6 to 25 oxyethylene groups, obtained from (meth)acrylic acid or a (meth)acrylic acid salt and from an oxyethylenated $C_{10}$-$C_{22}$ alcohol in an ethylene oxide mole ratio of 6 to 25.

Thus, as amphiphilic copolymers of 2-acrylamido-2-methylpropanesulfonic acid that may be used in the composition according to the invention, mention may be made in particular of polymers prepared from 2-acrylamido-2-methylpropanesulfonic acid or a sodium or ammonium salt thereof, with a (meth)acrylic acid ester and:
of a $C_{10}$-$C_{18}$ alcohol oxyethylenated in an ethylene oxide mole ratio of 8 (Genapol C-080 from the company Clariant),
of a $C_{11}$ oxo alcohol oxyethylenated in an ethylene oxide mole ratio of 8 (Genapol UD-080 from the company Clariant),
of a $C_{11}$ oxo alcohol oxyethylenated in an ethylene oxide mole ratio of 7 (Genapol UD-070 from the company Clariant),
of a $C_{12}$-$C_{14}$ alcohol oxyethylenated in an ethylene oxide mole ratio of 7 (Genapol LA-070 from the company Clariant),
of a $C_{12}$-$C_{14}$ alcohol oxyethylenated in an ethylene oxide mole ratio of 9 (Genapol LA-090 from the company Clariant),
of a $C_{12}$-$C_{14}$ alcohol oxyethylenated in an ethylene oxide mole ratio of 11 (Genapol LA-110 from the company Clariant),
of a $C_{16}$-$C_{18}$ alcohol oxyethylenated in an ethylene oxide mole ratio of 8 (Genapol T-080 from the company Clariant),
of a $C_{16}$-$C_{18}$ alcohol oxyethylenated in an ethylene oxide mole ratio of 11 (Genapol T-110 from the company Clariant),
of a $C_{16}$-$C_{18}$ alcohol oxyethylenated in an ethylene oxide mole ratio of 15 (Genapol T-150 from the company Clariant),
of a $C_{16}$-$C_{18}$ alcohol oxyethylenated in an ethylene oxide mole ratio of 20 (Genapol T-200 from the company Clariant),
of a $C_{16}$-$C_{18}$ alcohol oxyethylenated in an ethylene oxide mole ratio of 25 (Genapol T-250 from the company Clariant),
of a $C_{18}$-$C_{22}$ alcohol oxyethylenated in an ethylene oxide mole ratio of 25,
of a $C_{16}$-$C_{18}$ iso alcohol oxyethylenated in an ethylene oxide mole ratio of 25.

Even more preferably, the copolymer of 2-acrylamido-2-methylpropanesulfonic acid and of an alcohol (meth)acrylate is a copolymer of 2-acrylamido-2-methylpropanesulfonic acid and of a $C_{16}$-$C_{18}$ alcohol (meth)acrylate and more particularly oxyethylenated in an ethylene oxide mole ratio of 6 to 25, obtained from (meth)acrylic acid or a (meth)acrylic acid salt and from an oxyethylenated $C_{16}$-$C_{18}$ alcohol in an ethylene oxide mole ratio of 6 to 25.

Thus, as copolymer of 2-acrylamido-2-methylpropanesulfonic acid and of an alcohol (meth)acrylate, use will preferably be made in the composition according to the invention of polymers prepared from 2-acrylamido-2-methylpropanesulfonic acid as defined above or a sodium or ammonium salt thereof, with a (meth)acrylic acid ester and:
of a $C_{16}$-$C_{18}$ alcohol oxyethylenated in an ethylene oxide mole ratio of 8 (Genapol T-080 from the company Clariant),
of a $C_{16}$-$C_{18}$ alcohol oxyethylenated in an ethylene oxide mole ratio of 11 (Genapol T-110 from the company Clariant),
of a $C_{16}$-$C_{18}$ alcohol oxyethylenated in an ethylene oxide mole ratio of 15 (Genapol T-150 from the company Clariant),
of a $C_{16}$-$C_{18}$ alcohol oxyethylenated in an ethylene oxide mole ratio of 20 (Genapol T-200 from the company Clariant), of a $C_{16}$-$C_{18}$ alcohol oxyethylenated in an ethylene oxide mole ratio of 25 (Genapol T-250 from the company Clariant), of a $C_{16}$-$C_{18}$ iso alcohol oxyethylenated in an ethylene oxide mole ratio of 25.

Preferably, the copolymer of 2-acrylamido-2-methylpropanesulfonic acid and of an alcohol (meth)acrylate is a copolymer of 2-acrylamido-2-methylpropanesulfonic acid and of steareth-8 (meth)acrylate.

As preferred copolymer of 2-acrylamido-2-methylpropanesulfonic acid and of an alcohol (meth)acrylate according to the present invention, mention may be made of the non-crosslinked copolymer obtained from 92.65 mol % of 2-acrylamido-2-methylpropanesulfonic acid and 7.35 mol % of a $C_{16}$-$C_{18}$ alcohol (meth)acrylate comprising 8 oxyethylene groups (Genapol T-080), such as the product sold by the company Clariant under the name Aristoflex SNC 20®.

The copolymers of 2-acrylamido-2-methylpropanesulfonic acid and of an alcohol (meth)acrylate in accordance with the invention are preferentially partially or totally neutralized with a mineral base (for instance sodium hydroxide, potassium hydroxide or aqueous ammonia) or with an organic base such as monoethanolamine, diethanolamine, triethanolamine, an aminomethylpropanediol, N-methylglucamine, or basic amino acids, for instance arginine and lysine, and mixtures thereof The copolymers of 2-acrylamido-2-methylpropanesulfonic acid and of an alcohol (meth)acrylate used in the composition according to the invention are non-crosslinked.

Preferably, the amount of copolymer of 2-acrylamido-2-methylpropanesulfonic acid and of an alcohol (meth)acrylate as active material in the composition of the invention may range from 0.01% to 5% by weight, preferably from 0.05% to 3% by weight and better still from 0.1% to 1% by weight relative to the total weight of the composition.

Preferably, the ratio of the amount of oily phase to the amount of copolymer of 2-acrylamido-2-methylpropanesulfonic acid and of an alcohol (meth)acrylate as active material may range from 50 to 200 and preferably from 70 to 200.

Hydrophobic-modified Inulin-based Amphiphilic Polymer

A composition according to the invention also comprises at least one hydrophobic-modified inulin-based amphiphilic polymer.

According to the invention, the term "hydrophobic-modified inulin" especially means an inulin modified with hydrophobic chains, in particular modified by grafting hydrophobic chains onto the hydrophilic backbone of the said inulin.

Inulin is part of the fructan family.

Fructans or fructosans are oligosaccharides or polysaccharides comprising a sequence of anhydrofructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatic.

Fructans generally have a degree of polymerization from 2 to about 1000 and preferably from 2 to about 60.

Three groups of fructans are distinguished. The first group corresponds to products whose fructose units are for the most part linked via β-2-1 bonds. These are essentially linear fructans such as inulins.

The second group also corresponds to linear fructoses, but the fructose units are essentially linked via β-2-6 bonds. These products are levans.

The third group corresponds to mixed fructans, i.e. containing β-2-6 and β-2-1 sequences. These are essentially branched fructans, such as graminans.

Inulin may be obtained, for example, from chicory, dahlia or Jerusalem artichoke. In the context of the present invention, the hydrophobic-modified inulin is preferentially obtained from chicory.

The inulins used in the compositions according to the invention are hydrophobic-modified. In particular, they are obtained by grafting hydrophobic chains onto the hydrophilic backbone of the fructan.

The hydrophobic chains that may be grafted onto the main chain of the fructan may especially be linear or branched, saturated or unsaturated hydrocarbon-based chains containing from 1 to 50 carbon atoms, such as alkyl, arylalkyl, alkylaryl or alkylene groups; divalent cycloaliphatic groups or organopolysiloxane chains. These hydrocarbon-based or organopolysiloxane chains may especially comprise one or more ester, amide, urethane, carbamate, thiocarbamate, urea, thiourea and/or sulfonamide functions especially such as methylenedicyclohexyl and isophorone; or divalent aromatic groups such as phenylene.

According to a particular embodiment, the hydrophobic-modified inulin(s) used in the context of the invention are inulins bearing hydrophobic groups chosen from hydrophobic carbamate or ester groups.

The term "hydrophobic carbamate group" means a $C_4$-$C_{32}$ alkyl carbamate group, i.e. a group —OCONH—R, R being a $C_4$-$C_{32}$ alkyl.

The term "hydrophobic ester group" means a $C_4$-$C_{32}$ alkyl ester group, i.e. a group —OCO—R, R being a $C_4$-$C_{32}$ alkyl.

These hydrophobic groups are especially derived from the reaction of the hydroxyl groups of the starting inulin with either an isocyanate R—N=C=O (to form a carbamate group) or an acid R—COOH or acid chloride R—COCl (to form an ester group).

In particular, the inulin has a degree of polymerization from 2 to about 1000, preferably from 2 to about 100 and even more preferentially from 2 to about 70, and a degree of substitution of less than 2 on the basis of a fructose unit.

Advantageously, the hydrophobic carbamate group is a $C_6$-$C_{20}$ alkyl carbamate group. Preferably, the hydrophobic carbamate group is a $C_8$-$C_{18}$ alkyl carbamate group.

Preferentially, the hydrophobic carbamate group is a $C_{10}$-$C_{18}$ alkyl carbamate group. More preferentially, the hydrophobic carbamate group is a $C_{10}$-$C_{14}$ alkyl carbamate group.

According to a more preferred embodiment, the hydrophobic carbamate group is a lauryl carbamate group ($C_{12}$ alkyl group).

Inulins bearing hydrophobic carbamate groups are described, for example, in patent application WO 99/64549.

Advantageously, the hydrophobic ester group is a $C_6$-$C_{20}$ alkyl ester group. Preferably, the hydrophobic ester group is a $C_8$-$C_{20}$ alkyl ester group. Preferentially, the hydrophobic ester group is a $C_{10}$-$C_{20}$ alkyl ester group. More preferentially, the hydrophobic ester group is a $C_{10}$-$C_{18}$ alkyl ester group.

Inulins bearing hydrophobic ester groups are described, for example, in patent U.S. Pat. No. 5,877,144.

In particular, the hydrophobic groups of inulin are chosen from $C_4$-$C_{32}$ alkyl carbamate or $C_4$-$C_{32}$ alkyl ester groups, preferably from $C_{10}$-$C_{18}$ alkyl carbamate or $C_{10}$-$C_{18}$ alkyl ester groups.

Preferably, an inulin bearing hydrophobic carbamate groups is used.

The inulin bearing hydrophobic carbamate or ester groups may have a degree of substitution (proportion of OH of the inulin substituted with a hydrophobic group) ranging from 0.01 to 0.5, preferably ranging from 0.02 to 0.4 and preferentially ranging from 0.05 to 0.35. Advantageously, the degree of substitution may range from 0.1 to 0.3.

As examples of inulins bearing hydrophobic ester groups, mention may be made of stearoyl inulin, such as the products sold under the names Lifidrem INST® by the company Engelhard and Rheopearl INS® by the company Ciba; palmitoyl inulin; undecylenoyl inulin, such as the products sold under the names Lifidrem INUK® and Lifidrem INUM® by the company Engelhard.

An example of an inulin bearing hydrophobic carbamate groups that may be mentioned is inulin lauryl carbamate, such as the product sold under the name Inutec SP1® by the company Beneo.

Preferably, the hydrophobic-modified inulin in the composition of the invention is based on chicory inulin and in particular is inulin lauryl carbamate.

According to a particular embodiment, the amount of hydrophobic-modified inulin-based amphiphilic polymer as active material in the composition of the invention may range from 0.01% to 5% by weight, preferably from 0.05% to 3% by weight and preferably from 0.1% to 1% by weight relative to the total weight of the composition.

Preferably, the ratio of the amount of oily phase to the amount of hydrophobic-modified inulin-based amphiphilic polymer as active material may range from 50 to 200 and preferably from 50 to 150.

Emulsifiers

In order to facilitate the emulsification of the oily phase, the composition according to the invention may comprise one or more emulsifiers (other than the abovementioned polymers), also known as coemulsifiers.

The amount of emulsifier(s) as active material may range, for example, from 0.001% to 5% by weight, preferably from 0.005% to 2% by weight and better still from 0.01% to 2% by weight relative to the total weight of the composition.

The emulsifier is preferably used in a content of less than 20% by weight relative to the total weight of amphiphilic polymers.

The emulsifier may be chosen from alkylpolyglucosides, polyoxyethylene (POE) alkyl esters or ethers, glyceryl alkyl esters or ethers, oxyethylenated or non-oxyethylenated sorbitan alkyl esters or ethers, dimethicone copolyols, gemini emulsifiers and monosodium or disodium acylglutamates.

Mention may be made in particular of:
- glyceryl esters such as glyceryl monoalkyl or polyalkyl esters or ethers as described in documents EP 1 010 416 and EP 1 010 414, glyceryl monoisostearate, such as the product sold under the name Peceol Isostearique® by the company Gattefosse, polyglyceryl (4 mol) isostearate sold under the name Isolan GI 34® by the company Goldschmidt, polyglyceryl (3 mol) diisostearate sold under the name Lameform TGI® by the company Cognis and polyglyceryl (2 mol) distearate sold under the name Emalex PGSA® by the company Nihon Emulsion;
- polyethylene glycol esters and ethers, such as the polyethylene glycol alkyl esters and ethers as described in documents EP 1 120 101 and EP 1 016 453, oleth 50 sold under the name Emalex 550® by the company Nihon Emulsion, oleth 20 sold under the name Brij 98® by the company Uniqema, ceteth 2 and 10 sold under the names Brij 52® and 56® by the company Uniqema, laureth 23 sold under the name Brij 35® by the company Uniqema and PEG-8 stearate sold under the name Myrj 45® by the company Uniqema, PEG-8 isostearate such as the product sold under the name Prisorine 3644® by the company Uniqema, PEG-20 stearate and PEG-40 stearate sold under the names Myrj 49® and Myrj S2® by the company Uniqema. Mention may also be made of the following compounds sold by the company Uniqema: Brij 35®; Brij 30®; Brij 96®; Brij 56®; Brij 98®; Brij 76®; Brij 72®; Brij 52® and Brij 78® (corresponding INCI name: laureth 23; laureth 4; oleth 10; ceteth 10; oleth 20; steareth 10; steareth 2; ceteth 2 and steareth 20);
- sorbitan esters or ethers such as the oxyethylenated or non-oxyethylenated sorbitan monoalkyl or polyalkyl esters or ethers as described in document EP 1 010 415, or alternatively the following products sold by the company Uniqema: Tween 21®; Tween 40®; Tween 80®; Tween 60V® and Tween 61V (corresponding INCI name: Polysorbate 21; Polysorbate 40; Polysorbate 80; Polysorbate 60 and Polysorbate 61). Mention is also made of sorbitan isostearate such as the product sold under the name Arlacel 987® by the company Uniqema, sorbitan glyceryl isostearate such as the product sold under the name Arlacel 986® by the company Uniqema, sorbitan sesquioleate such as the product sold under the name Arlacel 83V® by the company Uniqema, sorbitan laurate, sorbitan monopalmitate, sorbitan oleate, sorbitan trioleate, sorbitan monostearate and sorbitan tristearate such as the products sold under the names Span 20®, Span 40®, Span 80V®, Span 85V®, Span 60® and Span 65V® by the company Uniqema;
- sugar monoalkyl or polyalkyl esters or ethers such as the sugar monoalkyl or polyalkyl esters or ethers as described in patent U.S. Pat. No. 6,689,371. Mention may be made, for example, of methylglucose isostearate such as Isolan-IS® from the company Degussa Goldschmidt or sucrose distearate such as Crodesta F50® sold by the company Croda, and sucrose stearate such as the Ryoto sugar ester S 1570® sold by the company Mitsubishi Kagaku Foods;
- siloxane polyethers such as Abil Care 85® (INCI name: BIS-PEG/PPG-16/16 PEG/PPG-16/16 dimethicone (and) caprylic/capric triglyceride) sold by the company Evonik;
- alkoxylated alkenyl succinates as described, for example, in document EP 1 025 898;
- fatty alcohols such as fatty alcohols containing from 8 to 26 carbon atoms, for instance cetyl alcohol, stearyl alcohol and a mixture thereof (cetearyl alcohol), octyldodecanol, 2-butyloctanol, 2-hexyldecanol, 2-undecylpentadecanol and oleyl alcohol, and mixtures thereof;
- silicone derivatives such as dimethicone copolyols, such as the mixture of cyclomethicone and of dimethicone copolyol sold under the name DC 5225 C® by the company Dow Corning, and alkyl dimethicone copolyols, such as the lauryl methicone copolyol sold under the name Dow Corning 5200 Formulation Aid® by the company Dow Corning and the cetyldimethicone copolyol sold under the name Abil EM 90® by the company Goldschmidt, or the polyglyceryl-4 isostearate/cetyl dimethicone copolyol/hexyl laurate mixture sold under the name Abil WE 90® by the company Goldschmidt;
- alkoxylated alkenyl succinates, for instance those described in document EP 1 025 898;
- phosphoric alkyl esters, for instance those described in document EP 1 013 338;

alkyl ether citrates, for instance those described in document EP 1 020 219;

lipoamino acids and salts thereof, such as monosodium and disodium acylglutamates, for instance monosodium stearoyl glutamate (Amisoft HS-11PF®) and disodium stearoyl glutamate (Amisoft HS-21P®) sold by the company Ajinomoto;

alkyl phosphates and salts thereof such as the alkali metal salts of dicetyl and of dimyristyl phosphate, or alternatively potassium cetyl phosphate such as Amphisol K® sold by the company DSM Nutritional Products;

cholesterol derivatives such as the alkali metal salts of cholesteryl sulfate and the alkali metal salts of cholesteryl phosphate;

the ammonium salts of phosphatidic acid;

phospholipids; and alkylsulfonic derivatives as described in patent EP 1 120 101.

According to a preferred mode of the invention, the coemulsifier is chosen from glyceryl esters (glyceryl isostearate), sorbitan esters (Polysorbate 60®), polyether siloxanes (Abil Care 85®) and polyethylene glycol esters (PEG-8® isostearate).

Aqueous Phase

The aqueous phase of the composition according to the invention comprises water and optionally one or more water-miscible or at least partially water-miscible compounds, for instance $C_2$ to $C_8$ lower polyols or monoalcohols, such as ethanol and isopropanol.

The term "polyol" should be understood as meaning any organic molecule comprising at least two free hydroxyl groups. Examples of polyols that may be mentioned include glycols, for instance butylene glycol, propylene glycol, and isoprene glycol, glycerol and polyethylene glycols, for instance PEG-8, sorbitol and sugars, for instance glucose.

The aqueous phase may also comprise any common water-soluble or water-dispersible additive as mentioned below.

The aqueous phase may represent from 30% to 98% by weight, preferably from 30% to 95% by weight, better still from 30% to 90% by weight and even better still from 35% to 85% by weight relative to the total weight of the composition.

The water-miscible compound(s), such as lower polyols and alcohols, may be present in an amount ranging from 0 to 30%, especially from 0.1% to 30% and better still in an amount ranging from 1% to 20%, relative to the total weight of the composition.

Oily phase

The nature of the oily phase of the emulsion according to the invention is not critical. The oily phase is a fatty phase comprising at least one fatty substance chosen from fatty substances that are liquid at room temperature and volatile or non-volatile oils of plant, mineral or synthetic origin, and mixtures thereof. These oils are physiologically acceptable.

The term "room temperature" should be understood as meaning a temperature of about 25° C., at normal atmospheric pressure (760 mmHg).

The oily phase may also comprise any common liposoluble or lipodispersible additive as mentioned below. It may especially comprise other fatty substances such as waxes, pasty compounds, fatty alcohols or fatty acids. The oily phase contains at least one oil, more particularly at least one cosmetic oil.

The term "oil" means a fatty substance that is liquid at room temperature.

Mention may be made, as oils which can be used in the composition of the invention, for example, of:

hydrocarbon-based oils of animal origin, such as perhydrosqualene;

hydrocarbon-based oils of plant origin, such as liquid fatty acid triglycerides comprising from 4 to 10 carbon atoms, for instance heptanoic or octanoic acid triglycerides, or alternatively, for example, sunflower oil, corn oil, soybean oil, marrow oil, grapeseed oil, sesame oil, hazelnut oil, apricot oil, macadamia oil, arara oil, coriander oil, castor oil, avocado oil, caprylic/capric acid triglycerides such as those sold by the company Stearineries Dubois or those sold under the names Miglyol 810®, 812® and 818® by the company Dynamit Nobel, jojoba oil and shea butter oil;

synthetic esters and ethers, in particular of fatty acids, such as the oils of formulae $R^1COOR^2$ and $R^1OR^2$ in which $R^1$ represents the residue of a fatty acid or of a fatty alcohol comprising from 8 to 29 carbon atoms and $R^2$ represents a branched or unbranched hydrocarbon-based chain comprising from 3 to 30 carbon atoms, such as, for example, purcellin oil, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate, and fatty alcohol heptanoates, octanoates and decanoates; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as volatile or non-volatile liquid paraffins, and derivatives thereof, petroleum jelly, polydecenes, isohexadecane, isododecane, and hydrogenated polyisobutene such as Parleam® oil;

partially hydrocarbon-based and/or silicone-based fluoro oils, such as those described in the document JP-A-2-295 912;

silicone oils, for instance volatile or non-volatile polymethylsiloxanes (PDMSs) containing a linear or cyclic silicone chain, which are liquid or pasty at room temperature, especially volatile silicone oils, in particular cyclopolydimethylsilo xanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsilo xydiphenylsilo xanes, diphenyl dimethicones, diphenylmethyldiphenyltrisilo xanes, 2-phenylethyltrimethylsilo xysilicates and polymethylphenylsilo xanes; and mixtures thereof.

According to a preferred embodiment, the composition of the invention comprises at least one oil chosen from silicone oils, linear or branched hydrocarbons, synthetic ethers and esters, and mixtures thereof and is especially chosen from volatile silicone oils and branched hydrocarbons, for instance Parlearn® oil, and mixtures thereof The amount of oily phase in the composition of the invention is less than 35% of the total weight of the composition and preferably less than or equal to 34% of the total weight of the composition.

The amount of oily phase may range, for example, from 5% to 35% by weight, preferably from 10% to 35% by weight and better still from 15% to 34% by weight, relative to the total weight of the composition.

As indicated above, this amount of oily phase does not comprise the amount of emulsifier.

Additives

In a known manner, the composition of the invention may also contain one or more adjuvants that are common in cosmetics or dermatology.

Examples of adjuvants that may be mentioned include gelling agents, active agents, preserving agents, antioxidants, fragrances, solvents, salts, fillers, sunscreens (=UV-screening agents), dyestuffs, basic agents (triethanolamine, diethanolamine or sodium hydroxide) or acidic agents (citric acid), and also lipid vesicles or any other type of vector (nanocapsules, microcapsules, etc.), and mixtures thereof.

These adjuvants are used in the usual proportions in the cosmetics field, for example from 0.01% to 30% of the total weight of the composition, and, depending on their nature, they are introduced into the aqueous phase of the composition or into the oily phase, or alternatively into vesicles or any other type of vector.

These adjuvants and the concentrations thereof must be such that they do not modify the desired properties for the emulsion of the invention.

Depending on the desired viscosity of the composition according to the invention, it is possible to incorporate therein one or more hydrophilic gelling agents.

Examples of hydrophilic gelling agents that may be mentioned include modified or unmodified carboxyvinyl polymers, such as the products sold under the names Carbopol® (INCI name: Carbomer) by the company Noveon; polyacrylamides, for instance Ultrez 10®, 20® and 21® from the company Lubrizol; optionally crosslinked and/or neutralized 2-acrylamido-2-methylpropanesulfonic acid polymers and copolymers, for instance the poly(2-acrylamido-2-methylpropanesulfonic acid) sold by the company Clariant under the name Hostacerin® (INCI name: ammonium polyacryldimethyltauramide); crosslinked anionic copolymers of acrylamide and of 2-acrylamido-2-methylpropanesulfonic acid, which are in the form of a W/O emulsion, such as those sold under the name Sepigel® 305 (CTFA name: Polyacrylamide/$C_{13-14}$ Isoparaffin/laureth-7) and under the name Simulgel® 600 (CTFA name: Acrylamide/Sodium acryloyldimethyltaurate copolymer/Isohexadecane/Polysorbate 80) by the company SEPPIC; polysaccharide biopolymers, for instance xanthan gum, guar gum, alginates and modified or unmodified celluloses; and mixtures thereof.

When they are present, these gelling agents must be introduced in an amount such that they do not modify the properties of the composition according to the invention.

Lipophilic gelling agents that may especially be mentioned include modified clays such as modified magnesium silicate (Bentone Gel VS38® from Rheox), or hectorite modified with distearyldimethylammonium chloride (INCI name: Disteardimonium hectorite) sold under the name Bentone 38 CE® by the company Rheox.

The gelling agent may be present in an active material content ranging from 0.05% to 10% by weight and preferentially from 0.1% to 5% by weight relative to the total weight of the composition.

Preferably, the gelling agent used in the composition according to the invention is xanthan gum.

In particular, a composition according to the present invention can comprise an elastomer.

According to a first embodiment, a composition according to the present invention comprises a silicone elastomer.

According to a second embodiment, a composition according to the present invention is free of silicone elastomer.

As fillers that may be used in the composition of the invention, examples that may be mentioned include the pigments such as titanium oxide, zinc oxide or iron oxide and organic pigments; kaolin; silica; talc; boron nitride; organic spherical powders, fibres; and mixtures thereof.

Examples of organic spherical powders that may be mentioned include polyamide powders and especially Nylon powders such as Nylon-1 or Polyamide 12, sold under the name Orgasol® by the company Atochem; polyethylene powders; Teflon; microspheres based on acrylic copolymers, such as Diakalytes (INCI name: Methylsilanol/Silicate Crosspolymer) or Rugby Balls (INCI name: Dimethiconol/Methylsilanol/Silicate Crosspolymer, sold by the company Takemoto Oil & Fat, under the respective names NLK 506® and NLK 602®; those made of ethylene glycol dimethacrylate/lauryl methacrylate copolymer sold by the company Dow Corning under the name Polytrap®; the expanded powders such as hollow microspheres, and especially the microspheres sold under the name Expancel® by the company Kemanord Plast or under the name Micropearl F80 ED® by the company Matsumoto; silicone resin microbeads such as those sold under the name Tospearl® by the company Toshiba Silicone; polymethyl methacrylate microspheres, sold under the name Microsphere M-100® or Microsphere M-310® by the company Matsumoto or under the name Covabead LH85® by the company Wackherr; ethylene-acrylate copolymer powders, such as those sold under the name Flobeads® by the company Sumitomo Seika Chemicals; powders of natural organic materials such as starch powders, especially of corn, wheat or rice starch, which may or may not be crosslinked, such as the starch powders crosslinked with octenylsuccinate anhydride, sold under the name Dry-Flo® by the company National Starch.

Mention may also be made of hydrophobic silicas such as Aerogel (INCI name: Silica Silylate) sold by the company Dow Corning under the name Dow Corning VM-2270 Aerogel Fine Particles®.

Examples of fibres that may be mentioned include polyamide fibres, especially such as Nylon 6 (or Polyamide 6) (INCI name: Nylon 6) fibres, Nylon 6,6 (or Polyamide 66) (INCI name: Nylon 66) fibres or Nylon 12 (INCI name: Nylon 12) fibres, or such as poly(p-phenylene terephthamide) fibres; and mixtures thereof.

These fillers may be present in amounts ranging from 0 to 20% by weight and preferably from 0.5% to 10% by weight relative to the total weight of the composition.

As active agents that may be used in the composition of the invention, examples that may be mentioned include moisturizers such as protein hydrolysates; sodium hyaluronate; polyols, for instance glycerol, glycols, for instance polyethylene glycols, and sugar derivatives; anti-inflammatory agents; procyannidol oligomers; vitamins, for instance vitamin A (retinol), vitamin E (tocopherol), vitamin K, vitamin C (ascorbic acid), vitamin B5 (panthenol), vitamin B3 or PP (niacinamide), derivatives of these vitamins (especially esters) and mixtures thereof; keratolytic agents and/or desquamating agents, such as salicylic acid and its derivatives, α-hydroxy acids, for instance lactic acid and glycolic acid and derivatives thereof, and ascorbic acid and its derivatives; urea; caffeine; depigmenting agents such as kojic acid, hydroquinone and caffeic acid; salicylic acid and its derivatives; retinoids such as carotenoids and vitamin A derivatives; hydrocortisone; melatonin; algal extracts, fungal extracts, plant extracts, yeast extracts or bacterial extracts; steroids; antibacterial active agents, for instance 2,4,4'-trichloro-2'-hydroxydiphenyl ether (or triclosan), 3,4,4'-trichlorocarbanilide (or triclocarban) and the acids indicated above, and especially salicylic acid and its derivatives; nucleotides such as adenosine; enzymes; flavonoids; tensioning agents such as synthetic polymers, plant proteins, polysaccharides of plant origin optionally in the form of microgels, starches, wax dispersions, mixed silicates and colloidal particles of mineral fillers; ceramides; anti-inflammatory agents; calmatives; mattifying agents; agents for preventing hair loss and/or for promoting regrowth of the hair; antiwrinkle active agents; essential oils; and mixtures thereof; and any active agent that is suitable for the final aim of the composition.

Preferably, the active agents used in the composition according to the invention are antiwrinkle active agents.

The UV-screening agents may be organic or mineral (or physical UV sunblocks).

They may be present in an active-material amount ranging from 0.01% to 20% by weight of active material, preferably from 0.1% to 20% by weight and better still 0.2% to 18% by weight relative to the total weight of the composition.

As examples of UV-A-active and/or UV-B-active organic screening agents that may be added to the composition of the invention, mention may be made of anthranilates; cinnamic derivatives; dibenzoylmethane derivatives; salicylic derivatives, camphor derivatives; triazine derivatives such as those described in patent applications U.S. Pat. No. 4,367,390, EP 1 863 145, EP 1 517 104, EP 1 570 838, EP 1 796 851, EP 1 775 698, EP 1 878 469 and EP 1 933 376; benzophenone derivatives; β,β'-diphenylacrylate derivatives; benzotriazole derivatives; benzimidazole derivatives; imidazo lines; bisbenzazolyl derivatives as described in patents EP 1 669 323 and U.S. Pat. No. 2,463,264; p-aminobenzoic acid (PABA) derivatives; methylenebis(hydroxyphenylbenzotriazole) derivatives as described in applications U.S. Pat. Nos. 5,237,071, 5,166,355, GB 2 303 549, DE 197 26 184 and EP 1 893 119; screening polymers and screening silicones such as those described in particular in application WO 93/04665; α-alkylstyrene-based dimers such as those described in patent application DE 198 55 649.

The total amount of organic UV-screening agents in the compositions according to the invention may range, for example, from 0.1% to 20% by weight relative to the total weight of the composition and preferably ranging from 0.2% to 18% by weight relative to the total weight of the composition.

As physical sunblocks that may be added to the composition of the invention, examples that may be mentioned include pigments and nanopigments of coated or uncoated metal oxides, especially titanium oxide, iron oxide, zirconium oxide, zinc oxide or cerium oxide, and mixtures thereof, these oxides possibly being in the form of optionally coated microparticles or nanoparticles (nanopigments).

The compositions of the invention are advantageously prepared according to a process in which the oily fatty phase, comprising the oils and optionally the other fatty substances, is emulsified in the aqueous phase (into which have been introduced the amphiphilic polymers), with gentle stirring, i.e. at a low degree of shear.

The stirring is preferably performed with a magnetic bar or any other stirring system which gives low stirring and is thus of low energy, at a temperature which may range from 20° C. to 45° C.

The term "low stirring" means stirring performed at a degree of shear of less than 1000 s$^{-1}$.

A subject of the invention is thus also a process for preparing the compositions as described above, in which the oily fatty phase is introduced into the aqueous phase, comprising the amphiphilic polymers, with low shear.

Thus, the emulsification process at low shear may be performed with any other stirring system that gives low stirring and is thus of low energy, for instance:
using a paddle or impeller,
with a turbomixer of the Moritz homogenizer type,
in a tank equipped with a tank-bottom turbomixer, a scraper blade, or a counter-rotating central mixing paddle and heating/cooling via the tank jacket. Examples that may be mentioned include the Macef and Maxilab tanks from the company Olsa, and the tanks sold by the company Pierre Guérin,
using a colloidal mill,
using a static emulsifier,
with an inline turbomixer, for example of IKA® or KMF® brand.

This process is a determining factor for obtaining large-sized oil globules in accordance with the invention.

A preparation method may be as follows: The fatty phase is prepared by stirring using a turbomixer, for 15 minutes at 3000 rpm. Separately, the aqueous phase and the preserving agents are heated to 80° C. with stirring at 1000 rpm for 10 minutes. The 2-acrylamido-2-methylpropanesulfonic acid polymer is then added with stirring at 3500 rpm for 10 minutes, and the copolymer of 2-acrylamido-2-methylpropanesulfonic acid and of an alcohol (meth)acrylate is then added. The mixture is left stirring at 3500 rpm for 30 minutes.

The mixture is cooled to 50° C. and the gelling agents are added with stirring at 3000 rpm for 15 minutes. The mixture is again cooled to room temperature (25° C.) and the fillers are then added. Finally, the fatty phase and the alcohol are added with stirring using a turbomixer at 3000 rpm for 10 to 15 minutes.

The compositions according to the invention may be, for example, in any of the galenical forms of O/W emulsions, for example in the form of a serum, a milk or a cream, and they are prepared according to the usual methods.

The compositions that are the subject of the invention are intended for topical application and can especially constitute a cosmetic composition intended, for example, for caring for (anti-wrinkle, anti-ageing, moisturizing, antisun, etc.), treating, cleansing and making up keratin materials, and especially human skin, lips, hair, eyelashes and nails.

Finally, a subject of the invention is a cosmetic process for treating keratin materials, characterized in that a cosmetic composition as defined above is applied to the said keratin materials.

The invention is illustrated in greater detail by the examples described below, which are given as non-limiting illustrations.

The percentages are weight percentages.

In the examples that follow, the weight percentages are indicated relative to the total weight of the composition.

EXAMPLE

Compositions 1 to 4 below were prepared:

| Compounds | Composition 1 outside the invention | Composition 2 according to the invention | Composition 3 outside the invention | Composition 4 outside the invention |
|---|---|---|---|---|
| Water | 53.95 | 53.65 | 53.65 | 53.45 |
| Glycerol | 7 | 7 | 7 | 7 |
| 2-Phenoxyethanol | 0.5 | 0.5 | 0.5 | 0.5 |
| Chlorphenesin | 0.25 | 0.25 | 0.25 | 0.25 |
| Disodium EDTA | 0.1 | 0.1 | 0.1 | 0.1 |

| Compounds | Composition 1 outside the invention | Composition 2 according to the invention | Composition 3 outside the invention | Composition 4 outside the invention |
|---|---|---|---|---|
| Inulin lauryl carbamate (Inutec SP1 ® from Beneo) | / | 0.3 | / | 0.6 |
| Copolymer of 2-acrylamido-2-methylpropanesulfonic acid and of steareth-8 methacrylate (Aristoflex SNC ® from Clariant) | 0.2 | 0.2 | 0.4 | / |
| 2-Acrylamido-2-methylpropanesulfonic acid polymer | 0.3 | 0.3 | 0.6 | 0.6 |
| Xanthan gum | 0.2 | 0.2 | / | / |
| Mica-titanium oxide-tin oxide | 0.5 | 0.5 | 0.5 | 0.5 |
| Methylsilanol/silicate crosspolymer | 1.5 | 1.5 | 1.5 | 1.5 |
| Polytetrafluoroethylene (PTFE) wax | 1.5 | 1.5 | 1.5 | 1.5 |
| Dimethicone (and) dimethiconol | 3 | 3 | 2 | 2 |
| Pentaerythrityl tetraoctanoate | 2 | 2 | 2 | 2 |
| Polysilicone-11 | 20 | 20 | 25 | 25 |
| Polydimethylsiloxane | 4 | 4 | / | / |
| Denatured ethyl alcohol | 5 | 5 | 5 | 5 |

Preparation Process

Compositions 1 to 4 were obtained according to the following protocol:

The fatty phase is prepared by mixing dimethicone (and) dimethiconol, Polysilicone-11 and pentaerythrityl tetraoctanoate with stirring using a turbomixer, for 15 minutes at 3000 rpm.

The aqueous phase and the preserving agents (2-phenoxyethanol and chlorphenesin) are heated to 80° C. with stirring at 1000 rpm for 10 minutes.

The Inutec SP1® is then added with stirring at 3500 rpm for 10 minutes, then the Aristoflex SNC® is added and is allowed to swell for 30 minutes.

The mixture is cooled to 50° C. and the gelling agents are added with stirring at 3000 rpm for 15 minutes.

The mixture is again cooled to room temperature (25° C.) and the fillers are then added.

Finally, the fatty phase and the denatured ethyl alcohol are added with stirring using a turbomixer at 3000 rpm for 10 to 15 minutes.

Evaluation of the Compositions

Compositions 1 and 2 are fluid and glidant on application.

Contrary to compositions 1, 2 and 3, the composition 4 does not contain "giant" drops. Furthermore, the composition 4 is not stable.

On application, composition 1, after a short aqueous "rupture", transforms into an oil with a silicone feel and leaves a film-forming greasy finish. There is no "quick-break" effect, no remanent freshness and no velvety finish.

Concerning the composition 3, it is not fluid and glidant on application. This composition is too thick. Furthermore, as for composition 1, there is no "quick-break" effect and no remanent freshness.

In contrast with compositions 1 and 3, composition 2 according to the invention "breaks" more in water on application. It affords a sensation of freshness and then transforms and thickens under the fingers without passing through an oily silicone stage.

In addition, composition 2 has a gelled feel which affords good glidance, and which gradually transforms into a silky and slightly silicone texture with great softness.

The final feel of the skin is pleasant, it combines great silky softness with a film-forming effect and also barely perceptible grip and tack.

Furthermore, composition 2 does not "fluff" at the time of application.

It leaves a soft, velvety aspect on the skin.

The invention claimed is:

1. Cosmetic composition, in the form of an oil-in-water emulsion, comprising at least:
   from 0.01% to 5% by weight of a 2-acrylamido-2-methylpropanesulfonic acid polymer, relative to the total weight of the composition,
   from 0.01% to 5% by weight of a non crosslinked copolymer of 2-acrylamido-2-methylpropanesulfonic acid and of an alcohol acrylate or an alcohol methacrylate, relative to the total weight of the composition, said non crosslinked copolymer comprising:
   (a) from 80 mol % to 99 mol % of 2-acrylamido-2-methylpropanesulfonic acid units of formula (I) below:

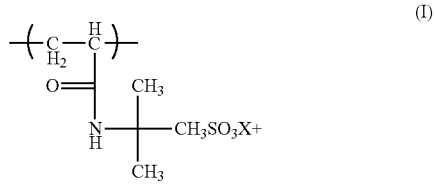

in which X+ is a proton, an alkali metal cation, an alkaline-earth metal cation, or an ammonium ion; and
   (b) from 1 mol % to 20 mol % of units of formula (II) below:

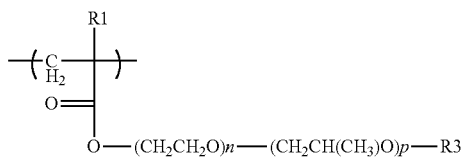

(II)

in which n and p, independently of each other, denote an integer ranging from 0 to 30, with the proviso that n+p ranges from 1 to 30, $R_1$ denotes a hydrogen atom or a linear or branched $C_1$-$C_6$ alkyl radical, and $R_3$ denotes a linear or branched alkyl group comprising m carbon atoms, with m ranging from 6 to 30, and from 0.01% to 5% by weight of a hydrophobic-modified inulin-based amphiphilic polymer, relative to the total weight of the composition, the globules of the said emulsion having a mean size ranging from 15 to 500 microns and the oily phase being present in an amount of less than 35% by weight relative to the total weight of the composition.

2. Composition according to claim 1, wherein the copolymer of 2-acrylamido-2-methylpropanesulfonic acid and of an alcohol (meth)acrylate is a copolymer of 2-acrylamido-2-methylpropanesulfonic acid and of a $C_{16}$-$C_{18}$ alcohol (meth)acrylate.

3. Composition according to claim 1, wherein the hydrophobic groups of inulin are chosen from $C_4$-$C_{32}$ alkyl carbamate or $C_4$-$C_{32}$ alkyl ester groups.

4. Composition according to claim 1, wherein the hydrophobic-modified inulin-based amphiphilic polymer is based on chicory inulin.

5. Composition according to claim 1, wherein the oily phase is present in an amount of between 5% and 35% by weight, relative to the total weight of the composition.

6. Composition according to claim 1, wherein a weight ratio of the amount of oily phase to the amount of 2-acrylamido-2-methylpropanesulfonic acid polymer as active material is between 40 and 200.

7. Composition according to claim 1, wherein a weight ratio of the amount of oily phase to the amount of copolymer of 2-acrylamido-2-methylpropanesulfonic acid and of an alcohol (meth)acrylate as active material is between 50 and 200.

8. Composition according to claim 1, wherein a weight ratio of the amount of oily phase to the amount of hydrophobic-modified inulin-based amphiphilic polymer as active material is between 50 and 200.

9. Composition according to claim 1, wherein the mean size of the globules of the said emulsion is between 15 and 300 microns.

10. Composition according to claim 1, also containing at least one gelling agent.

11. Process for preparing a cosmetic composition, in the form of an oil-in-water emulsion, comprising introducing the oily phase into the aqueous phase, with low shear, the composition comprising at least:

from 0.01% to 5% by weight of a 2-acrylamido-2-methylpropanesulfonic acid polymer, relative to the total weight of the composition, from 0.01% to 5% by weight of a non crosslinked copolymer of 2-acrylamido-2-methylpropanesulfonic acid and of an alcohol acrylate or an alcohol methacrylate, relative to the total weight of the composition, said non crosslinked copolymer comprising:

(a) from 80 mol % to 99 mol % of 2-acrylamido-2-methylpropanesulfonic acid units of formula (I) below:

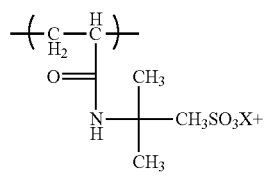

(I)

in which $X^+$ is a proton, an alkali metal cation, an alkaline-earth metal cation, or an ammonium ion; and (b) from 1 mol % to 20 mol % of units of formula (II) below:

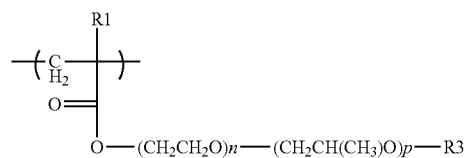

(II)

in which n and p, independently of each other, denote an integer ranging from 0 to 30, with the proviso that n+p ranges from 1 to 30, $R_1$ denotes a hydrogen atom or a linear or branched $C_1$-$C_6$ alkyl radical, and $R_3$ denotes a linear or branched alkyl group comprising m carbon atoms, with m ranging from 6 to 30, and from 0.01% to 5% by weight of a hydrophobic-modified inulin-based amphiphilic polymer, relative to the total weight of the composition, the globules of the said emulsion having a mean size ranging from 15 to 500 microns and the oily phase being present in an amount of less than 35% by weight relative to the total weight of the composition.

12. Cosmetic process for treating keratin materials, wherein a cosmetic composition, in the form of an oil-in-water emulsion, is applied to the said keratin materials, the composition comprising at least:

from 0.01% to 5% by weight of a 2-acrylamido-2-methylpropanesulfonic acid polymer, relative to the total weight of the composition, from 0.01% to 5% by weight of a non crosslinked copolymer of 2-acrylamido-2-methylpropanesulfonic acid and of an alcohol acrylate or an alcohol methacrylate, relative to the total weight of the composition, said non crosslinked copolymer comprising:

(a) from 80 mol % to 99 mol % of 2-acrylamido-2-methylpropanesulfonic acid units of formula (I) below:

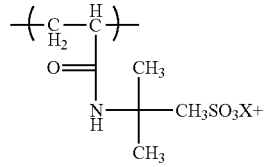

(I)

in which $X^+$ is a proton, an alkali metal cation, an alkaline-earth metal cation, or an ammonium ion; and
(b) from 1 mol % to 20 mol % of units of formula (II) below:

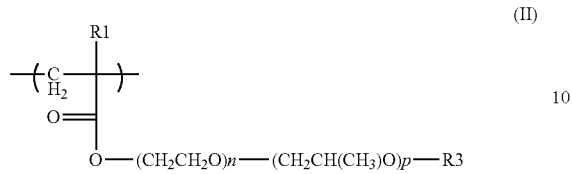

(II)

in which n and p, independently of each other, denote an integer ranging from 0 to 30, with the proviso that n+p ranges from 1 to 30, $R_1$ denotes a hydrogen atom or a linear or branched $C_1$-$C_6$ alkyl radical, and $R_3$ denotes a linear or branched alkyl group comprising m carbon atoms, with m ranging from 6 to 30, and from 0.01% to 5% by weight of a hydrophobic-modified inulin-based amphiphilic polymer, relative to the total weight of the composition, the globules of the said emulsion having a mean size ranging from 15 to 500 microns and the oily phase being present in an amount of less than 35% by weight relative to the total weight of the composition.

* * * * *